US 10,188,720 B2
(12) United States Patent
Esaki et al.

(10) Patent No.: US 10,188,720 B2
(45) Date of Patent: Jan. 29, 2019

(54) RECOMBINANT MAREK'S DISEASE VIRUSES AND USES THEREOF

(71) Applicant: Ceva Sante Animale, Libourne (FR)

(72) Inventors: Motoyuki Esaki, Saitama (JP); Shuji Saitoh, Yokohama (JP); Takanori Sato, Kanagawa (JP)

(73) Assignee: CEVA SANTE ANIMALE, Libourne (FR)

(*) Notice: Subject to any disclaimer, the term of this patent is extended or adjusted under 35 U.S.C. 154(b) by 0 days.

(21) Appl. No.: 14/915,534

(22) PCT Filed: Sep. 5, 2014

(86) PCT No.: PCT/EP2014/068964
§ 371 (c)(1),
(2) Date: Feb. 29, 2016

(87) PCT Pub. No.: WO2015/032910
PCT Pub. Date: Mar. 12, 2015

(65) Prior Publication Data
US 2016/0220657 A1    Aug. 4, 2016

(30) Foreign Application Priority Data
Sep. 6, 2013    (EP) .................................... 13183393

(51) Int. Cl.
| *A61K 39/12* | (2006.01) |
| *A61K 39/255* | (2006.01) |
| *C12N 7/00* | (2006.01) |
| *C12N 15/86* | (2006.01) |
| *A61K 39/17* | (2006.01) |
| *C07K 14/005* | (2006.01) |
| *A61K 39/00* | (2006.01) |

(52) U.S. Cl.
CPC .............. *A61K 39/12* (2013.01); *A61K 39/17* (2013.01); *C07K 14/005* (2013.01); *C12N 7/00* (2013.01); *C12N 15/86* (2013.01); *A61K 2039/5256* (2013.01); *A61K 2039/552* (2013.01); *A61K 2039/70* (2013.01); *C12N 2710/16321* (2013.01); *C12N 2710/16334* (2013.01); *C12N 2710/16343* (2013.01); *C12N 2710/16351* (2013.01); *C12N 2710/16371* (2013.01); *C12N 2720/10034* (2013.01); *C12N 2720/10051* (2013.01); *C12N 2720/10071* (2013.01); *C12N 2760/16034* (2013.01); *C12N 2760/18134* (2013.01)

(58) Field of Classification Search
None
See application file for complete search history.

(56) References Cited

U.S. PATENT DOCUMENTS

| 6,632,664 B1* | 10/2003 | Saitoh ................... C12N 15/86 424/199.1 |
| 6,764,684 B2* | 7/2004 | Saitoh ................... A61K 39/12 424/199.1 |
| 6,866,852 B2* | 3/2005 | Saitoh ................. C07K 14/005 424/199.1 |
| 2005/0244431 A1 | 11/2005 | Saito et al. |

FOREIGN PATENT DOCUMENTS

| EP | 1298139 A2 | 4/2003 |
| EP | 1731612 A1 | 12/2006 |
| EP | 2644702 A1 | 10/2013 |
| WO | WO-03/064595 A2 | 8/2003 |
| WO | WO-2010/119112 A1 | 10/2010 |
| WO | WO-2013/057235 A1 | 4/2013 |
| WO | WO-2013/057236 A1 | 4/2013 |

OTHER PUBLICATIONS

Tsukamoto et al "Complete, Long-Lasting Protection Against Lethal Infectious Bursal Disease Virus Challenge by a Single Vaccination with an Avian Herpesvirus Vector Expressing VP2 Antigens" Journal of Virology vol. 76, pp. 5637-5645, 2002.
Tsukamoto et al "Protection of Chickens Against Very Virulent Infectious Bursal Disease Virus (IBDV) and Marek's Disease Virus (MDV) with a Recombinant MDV Expressing IBDV VP2" Virology vol. 257, pp. 352-362, 1999.
Zhou et al "Protection of Chickens, with or without Maternal Antibodies, Against IBDV Infection by a Recombinant IBDV-VP2 Protein" Vaccine vol. 28, pp. 3990-3996, 2010.

* cited by examiner

*Primary Examiner* — Stacy B Chen
(74) *Attorney, Agent, or Firm* — Cesari and McKenna, LLP

(57) ABSTRACT

The present invention relates recombinant viruses and the uses thereof. More particularly, the invention relates to novel recombinant Marek's disease viruses encoding polypeptide (s) of interest, and their use to express or deliver such polypeptides to animals, particularly poultry. The invention is particularly suited to vaccinate poultry against avian pathogens.

20 Claims, 8 Drawing Sheets

Specification includes a Sequence Listing.

M: Precision Plus Protein All Blue Standards (Bio-Rad, Cat# 161-0373)
1: CEF control
2: Wild type Rispens
3: RR013 Clone 1
4: RR013 Clone 2
5: RR024
6: RR030 Clone 1
7: RR030 Clone 2
8: RR030 Clone 3
9: RR031 Clone 1
10: RR031 Clone 2

Figure 4

IBDV ELISA Titer

[Graph: S/P Value (y-axis, 0 to 1.2) vs Weeks (x-axis, 0 to 7)]

- RR013
- RR024
- RR025
- FW023
- NINC
- NICC

IDEXX IBD Ab Test: IDEXX Laboratories

RR013: Rispens/US2/Bac-VP2stc
RR024: Rispens/US2/RSV-VP2stc
RR025: Rispens/US2/SV40-VP2stc
FW023 (recombinant HVT/IBD control): HVT/UL45-46/Bac-VP2stc
NINC = non-immunized, non-challenged negative controls
NICC = non-immunized, challenged positive controls

Figure 5

IBDV ELISA TITER

[Chart: S/P Value vs Weeks of age (1-7), showing curves for NICC, RR013, RR030, RR031, FW023]

IDEXX IBD Ab Test: IDEXX Laboratories

NICC = non-immunized, challenged positive controls
RR013: Rispens/US2/Bac-VP2stc
RR030: Rispens/US2/Coa5-VP2stc
RR031: Rispens/US2/Coa5-VP2stc2
FW023 (recombinant HVT/IBD control): HVT/UL45-46/Bac-VP2stc IDEXX IBD Ab Test: IDEXX Laboratories NICC = non-immunized, challenged positive controls
RR030: Rispens/US2/Coa5-VP2stc
FW029 (recombinant HVT/ND control): HVT/UL45-46/Pec-F
FW023 (recombinant HVT/IBD control): HVT/UL45-46/Bac-VP2stc IDEXX NDV Ab Test: IDEXX Laboratories NICC = non-immunized, challenged positive controls
RR030: Rispens/US2/Coa5-VP2stc
FW029 (recombinant HVT/ND control): HVT/UL45-46/Pec-F

```
                        SEQUENCE LISTING

<160> NUMBER OF SEQ ID NOS: 12

<210> SEQ ID NO 1
<211> LENGTH: 35
<212> TYPE: DNA
<213> ORGANISM: Artificial sequence
<220> FEATURE:
<223> OTHER INFORMATION: primer

<400> SEQUENCE: 1
aaacgaattc gaagcttgca tgccccgcta aggac                                35

<210> SEQ ID NO 2
<211> LENGTH: 46
<212> TYPE: DNA
<213> ORGANISM: Artificial sequence
<220> FEATURE:
<223> OTHER INFORMATION: primer

<400> SEQUENCE: 2
gccaccagat ggaactgggg ccaataaggc cggtatgccg tgggcc                    46

<210> SEQ ID NO 3
<211> LENGTH: 46
<212> TYPE: DNA
<213> ORGANISM: Artificial sequence
<220> FEATURE:
<223> OTHER INFORMATION: primer

<400> SEQUENCE: 3
ggcccacggc ataccggcct tattggcccc agttccatct ggtggc                    46

<210> SEQ ID NO 4
<211> LENGTH: 34
<212> TYPE: DNA
<213> ORGANISM: Artificial sequence
<220> FEATURE:
<223> OTHER INFORMATION: primer

<400> SEQUENCE: 4
gattacgaat tcgcccttt acatgctgcc ccaa                                  34

<210> SEQ ID NO 5
<211> LENGTH: 274
<212> TYPE: DNA
<213> ORGANISM: Artificial sequence
<220> FEATURE:
<223> OTHER INFORMATION: Core sequence of chicken beta-actin promoter

<400> SEQUENCE: 5
tattttgtgc agcgatgggg gcggggggg ggggggcgcg cgccaggcgg ggcggggcgg      60
ggcgaggggc ggggcggggc gaggcggaga ggtgcggcgg cagccaatca gagcggcgcg    120
ctccgaaagt ttccttttat ggcgaggcgg cggcggcggc ggccctataa aaagcgaagc    180
```

```
gcgcggcggg cgggagtcgc tgcgcgctgc cttcgcccccg tgccccgctc cgccgccgcc    240
tcgcgccgcc cgccccggct ctgactgacc gcgt                                 274
```

<210> SEQ ID NO 6
<211> LENGTH: 20
<212> TYPE: DNA
<213> ORGANISM: Artificial sequence
<220> FEATURE:
<223> OTHER INFORMATION: primer

<400> SEQUENCE: 6

```
gtggggaccc gaggattttg                                                  20
```

<210> SEQ ID NO 7
<211> LENGTH: 52
<212> TYPE: DNA
<213> ORGANISM: Artificial sequence
<220> FEATURE:
<223> OTHER INFORMATION: primer

<400> SEQUENCE: 7

```
gcgtctagag gatcgatcca ccggtcgcca ccatgacaaa cctgcaagat ca              52
```

<210> SEQ ID NO 8
<211> LENGTH: 24
<212> TYPE: DNA
<213> ORGANISM: Artificial sequence
<220> FEATURE:
<223> OTHER INFORMATION: primer

<400> SEQUENCE: 8

```
tgaactacac aaaattgata ctga                                             24
```

<210> SEQ ID NO 9
<211> LENGTH: 20
<212> TYPE: DNA
<213> ORGANISM: Artificial sequence
<220> FEATURE:
<223> OTHER INFORMATION: primer

<400> SEQUENCE: 9

```
gaggcggacg taaatggaga                                                  20
```

<210> SEQ ID NO 10
<211> LENGTH: 24
<212> TYPE: DNA
<213> ORGANISM: Artificial sequence
<220> FEATURE:
<223> OTHER INFORMATION: primer

<400> SEQUENCE: 10

```
gccagggaat ccagggaaaa agac                                             24
```

<210> SEQ ID NO 11
<211> LENGTH: 21
<212> TYPE: DNA
<213> ORGANISM: Artificial sequence
<220> FEATURE:
<223> OTHER INFORMATION: primer

<400> SEQUENCE: 11

```
tatgagcggc agttatcgtg t                                                21
```

<210> SEQ ID NO 12
<211> LENGTH: 1506

```
<212> TYPE: DNA
<213> ORGANISM: Artificial sequence
<220> FEATURE:
<223> OTHER INFORMATION: chicken beta actin promoter

<400> SEQUENCE: 12
tgcagctcag tgcatgcacg ctcattgccc atcgctatcc ctgcctctcc tgctggcgct    60
ccccgggagg tgacttcaag gggaccgcag gaccacctcg ggggtggggg gagggctgca   120
cacgcggacc ccgctccccc tccccaacaa agcactgtgg aatcaaaaag ggggagggg    180 ggatggaggg gcgcgtcaca ccccgcccc acaccctcac ctcgaggtga gccccacgtt   240
ctgcttcact ctccccatct ccccccctc cccaccccca attttgtatt tatttatttt    300
ttaattattt tgtgcagcga tgggggcggg ggggggggg gcgcgcgcca ggcggggcgg    360
ggcggggcca ggggcggggc ggggcgaggc ggagaggtgc ggcggcagcc aatcagagcg   420
gcgcgctccg aaagtttcct tttatggcga ggcggcggcg gcggcggccc tataaaaagc   480
gaagcgcgcg gcgggcggga gtcgctgcgc gctgccttcg ccccgtgccc cgctccgccg   540
ccgcctcgcg ccgcccgccc cggctctgac tgaccgcgtt actcccacag gtgagcgggc   600
gggacggccc ttctcctccg ggctgtaatt agcgcttggt ttaatgacgg ctcgtttctt    660
ttctgtggct gcgtgaaagc cttaaagggc tccgggaggc ccctttgtgc ggggggagc    720 ggctcggggg gtgcgtgcgt gtgtgtgtgc gtgggagcg ccgcgtgcgg ctccgcgctg    780
cccggcggct gtgagcgctg cgggcgcggc gcggggcttt gtgcgctccg cagtgtgcgc   840
gaggggagcg cggccggggg cggtgccccg cggtgcgggg ggggctgcga ggggaacaaa   900
ggctgcgtgc ggggtgtgtg cgtggggggg tgagcagggg gtgtgggcgc ggcggtcggg   960 ctgtaaccccc ccctgcacc ccctccccg aagttgctga gcacggcccg gcttcgggtg   1020
cggggctccg tgcgggcgt ggcgcggggc tcgccgtgcc gggcggggg tggcggcagg   1080 tgggggtgcc gggcggggcg gggccgcctc gggccggga gggctcgggg gaggggcgcg  1140 gcggccccg gagcgccggc ggctgtcgag gcgcggcgag ccgcagccat tgcctttat    1200 ggtaatcgtg cgagagggcg cagggacttc ctttgtccca aatctgtgcg gagccgaaat   1260
ctgggaggcg ccgccgcacc ccctctagcg ggcgcggggc gaagcggtgc ggcgccggca   1320
ggaaggaaat gggcggggag ggccttcgtg cgtcgccgcg ccgccgtccc cttctccatc   1380
tccagcctcg gggctgtccg caggggggacg gctgccttcg ggggggacgg ggcagggcgg   1440
ggttcggctt ctggcgtgtg accggcgggg tttatatctt cccttctctg ttcctccgca   1500
gccccc                                                             1506
```

RECOMBINANT MAREK'S DISEASE VIRUSES AND USES THEREOF

CROSS REFERENCE TO RELATED APPLICATIONS

This application is the National Stage of International Application No. PCT/EP2014/068964, filed on Sep. 5, 2014, which claims the benefit of European Application No. 13183393.1, filed on Sep. 6, 2013. The contents of both applications are hereby incorporated by reference in their entirety.

FIELD OF THE INVENTION

The present invention relates to recombinant viruses and the uses thereof. More particularly, the invention relates to novel recombinant Marek's disease viruses encoding polypeptide(s) of interest, and their use to express or deliver such polypeptides to animals, particularly poultry. The invention is particularly suited to vaccinate poultry against avian pathogens.

BACKGROUND OF THE INVENTION

Poultry meat and eggs are important food sources, whose consumption increases continually due to the growth of the human population and their great quality-price ratio. The recent epidemic of avian influenza focused the public opinion on poultry health as well as food safety and security. Poultry vaccine technology became a worldwide concern.

Recombinant viruses expressing pathogen proteins are commonly used as poultry vaccines against targeted pathogens. Vaccines including such viruses induce expression of foreign pathogen proteins or fragments thereof within infected cells, which can subsequently induce a specific and protective humoral immunity as well as cell-mediated immunity.

It is known that different viruses can survive in the body of an infected animal in the state of latent or persistent infection. Consequently, such viruses, in which a foreign gene derived from a pathogen has been integrated, have been developed to be used as viral-vectored vaccines increasing the duration of immunity to an immunized animal.

These viral vectors (or recombinant viruses) are based typically on avipox viruses, such as fowlpox (EP-A-0,517, 292), herpes virus, such as Marek's disease virus serotypes 1, 2 and 3 (HVT) (e.g., WO-A-87/04463, 5,980,906, 5,853, 733) or, alternatively, Newcastle disease virus (NDV) and avian adenoviruses.

These recombinant avian viruses display variable levels of protection. A recombinant HVT expressing IBDV VP2 has shown advantages over classical IBD vaccines (Vectormune® IBD). Other HVT vectors of interest express NDV (Vectormune® ND) or ILTV (Vectormune® LT) antigens.

One of the practical problems of HVT-based recombinant viruses is their interference when several viruses are used in combination to confer immunogenicity against distinct pathogens. Indeed, when two distinct rHVT expressing different antigens are mixed, a lower protection is caused at least against one of the disease (see e.g., Slacum G et al., 2009, The compatibility of HVT recombinants with other Marek's disease vaccines, 58th Western Poultry Disease Conference, Sacramento, Calif., USA, March 23-25, p 84).

Accordingly, there is a need for new approaches to improve vaccination in animals, particularly in poultry, allowing concomitant protection against several diseases.

Multivalent HVT vectors have been developed which can express two distinct antigenic peptides (see PCT/EP2013/056839).

The present invention discloses novel recombinant viruses suitable to induce strong immune protection in animals and which may, in addition, be used in combination with other viral vaccines to procure extended immunity.

SUMMARY OF THE INVENTION

The present invention relates to recombinant Marek's disease viruses ("MDV") which can encode one or several polypeptide(s) of interest. The invention more specifically discloses improved MDV viruses comprising a beta-actin derived promoter and surprisingly shows that, within the context of these viruses, such constructs allow highly improved expression and induction of strong protective immunity. The invention further shows that such viruses are compatible for combined use with distinct avian herpes viruses, to induce improved immune response against distinct antigenic pathogens without substantial cross-interference.

An object of the invention therefore resides in a recombinant Marek's disease virus ("rMDV") which comprises a recombinant nucleotide sequence encoding a polypeptide of interest operably linked to a promoter derived from a chicken beta-actin promoter.

A further object of the invention is a recombinant Marek's disease virus which comprises (1) a promoter comprising a core sequence of a chicken beta-actin promoter and (2) under the control of said promoter, a recombinant nucleotide sequence encoding a polypeptide.

The recombinant nucleotide sequence may be inserted in various regions of the viral genome, preferably in a region that is non-essential for viral replication or infection, preferably into the US2 gene. As will be discussed, the rMDV of the invention may comprise one or several recombinant nucleotide sequences encoding distinct polypeptides of interest. The polypeptide of interest is more particularly an antigenic peptide, typically an antigenic peptide of an avian pathogen. The recombinant Marek's disease virus (rMDV) of the invention is preferably of serotype 1 (MDV1).

Another object of the invention resides in a composition comprising a recombinant Marek's disease virus as defined above and, optionally, a pharmaceutically or veterinary acceptable excipient or carrier and/or a suitable adjuvant.

A further object of the invention relates to a vaccine composition comprising a recombinant Marek's disease virus as defined above. Such a vaccine can be used e.g., for immunizing avians, such as poultry.

Another object of the invention resides in a recombinant Marek's disease virus or composition as defined above for use to vaccinate an avian, preferably a chicken.

Another object of the invention resides in a recombinant Marek's disease virus or composition as defined above for use to induce or stimulate an immune response in an avian, preferably a chicken.

A further object of the invention is a recombinant MDV1 as defined above, for use in combination with a further recombinant herpes virus of a distinct serotype and expressing a distinct antigen, to vaccinate an avian, preferably a chicken, by simultaneous, separate sequential or alternated administration.

In another aspect, the invention provides a method of vaccinating an animal comprising at least one administration of a composition or virus as defined above.

In a further aspect, the invention provides a method for inducing an immunogenic or protective response in an animal against one or more avian pathogens comprising at least one administration of a composition or virus as defined above.

A further object of the invention is a method for producing a recombinant Marek's disease virus comprising (i) the introduction of a recombinant nucleotide sequence encoding a polypeptide under the control of a promoter comprising a core sequence of a chicken beta-actin promoter into a nonessential region of the genome of a Marek's disease virus, (ii) optionally replicating the virus and, (iii) optionally collecting the virus.

A further object of the invention relates to a recombinant nucleic acid molecule comprising the genome of a Marek's disease virus or a fragment thereof, wherein said genome or fragment comprises a US2 gene modified by insertion of a recombinant nucleotide sequence comprising a sequence encoding a polypeptide under the control of a promoter comprising a core sequence of a chicken beta-actin promoter.

The invention also relates to a plasmid comprising a nucleic acid molecule as defined above.

Another object of the invention is a host cell, or a culture of such cells, comprising a nucleic acid molecule or a plasmid or a virus as defined above.

The invention further relates to method of immunizing an avian comprising administering to said avian an effective immunizing amount of a vaccine or composition or virus of the invention.

The invention further provides a vaccination kit for immunizing an avian which comprises an effective amount of a vaccine of the invention and a means for administering said vaccine to said avian.

The invention may be used for expressing a polypeptide in any animal, preferably for the vaccination of an avian, and it is suitable for expressing any polypeptide or peptide, specifically any immunogenic peptide of avian pathogens.

LEGEND TO THE FIGURES

FIG. 4 illustrates IBDV ELISA titers in SPF chickens vaccinated with recombinant Rispens/IBD using a commercial IBD ELISA kit.

FIG. 5 illustrates IBDV ELISA titers in commercial white leghorn chickens vaccinated with recombinant Rispens/IBD using a commercial IBD ELISA kit

DETAILED DESCRIPTION OF THE INVENTION

Figure 1:
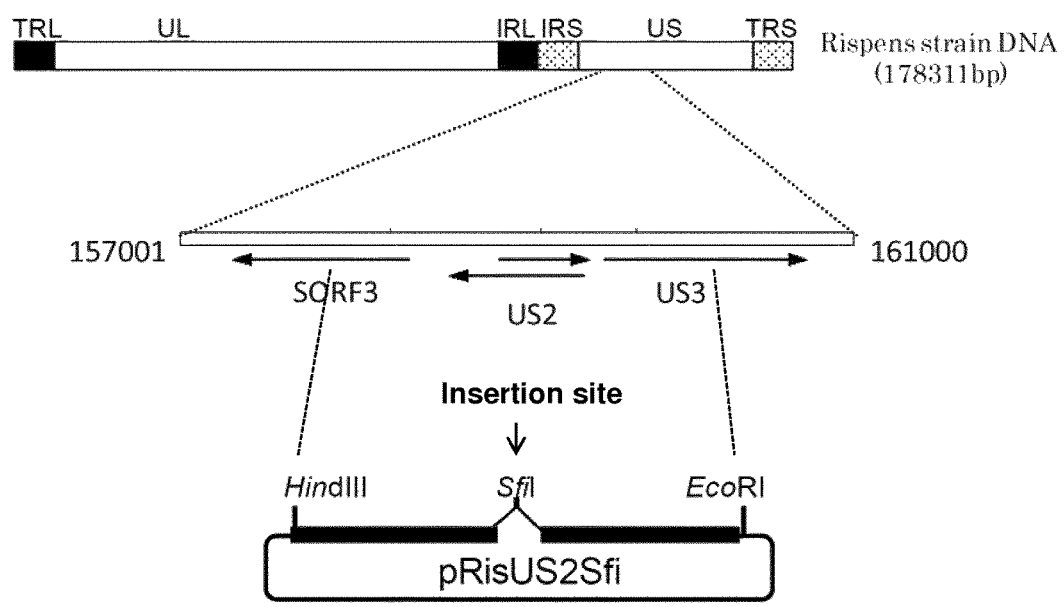
FIG. 1 illustrates a schematic diagram of the Rispens genome and the location of the cloned region including the insertion site within the US2 gene.
Figure 2:
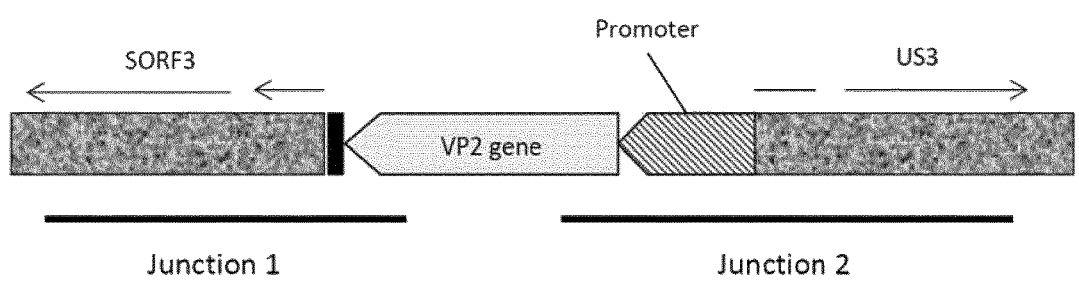
FIG. 2 shows a diagram of recombinant Rispens/IBD genome, indicating locations of Junction 1 and Junction 2 amplified in PCR reactions to confirm the genome structures of the viruses.
Figure 3:
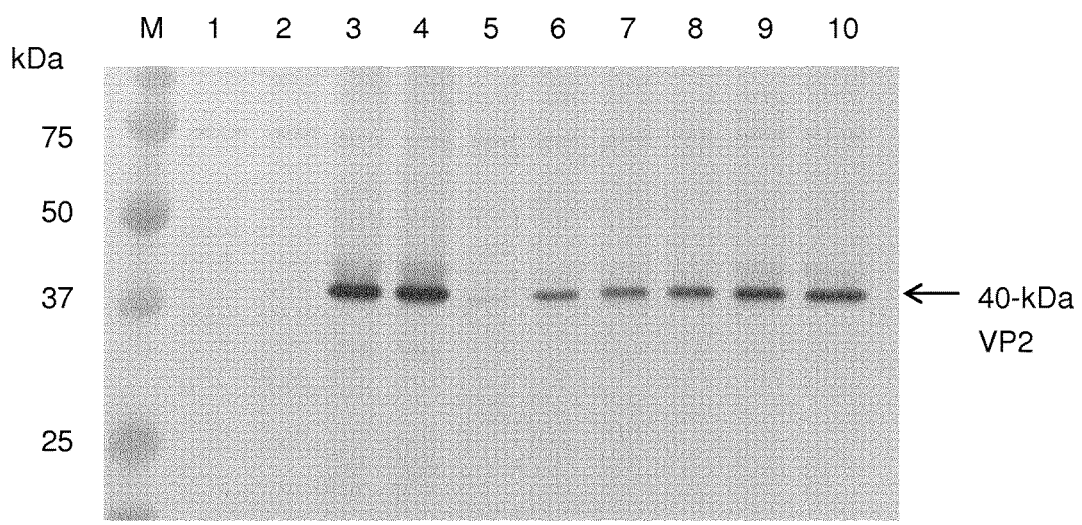
FIG. 3 is a western blot assay detecting expression of IBDV VP2 protein by the recombinant Rispens/IBD viruses.

The present invention generally relates to rMDV which comprise a recombinant nucleotide sequence encoding a product of interest placed under the transcriptional control of a chicken beta actin-derived promoter. The present invention also relates to compositions comprising such rMDV, as well as to the use thereof for vaccination of animals, particularly poultry.

The present disclosure will be best understood by reference to the following definitions:

Definitions

The term "virus" designates in particular a viral particle comprising a nucleic acid molecule (e.g., a genome) encapsulated in a capsid or capsule. The term "virus" also designates a viral vector or an isolated viral genome.

The term "recombinant" designates a molecule which has been created, designed or modified using genetic technologies. In relation to a virus, the term more specifically designates a virus whose genome has been modified by insertion of at least one heterologous nucleic acid, i.e., a nucleic acid (e.g., DNA) which is not found naturally in the genome of the virus, or which is found naturally in said genome but in a different form or at a different position. A recombinant virus can be manufactured by a variety of methods and, once made, can be reproduced without further use genetic technologies. In relation to a nucleic acid (e.g., a gene), the term "recombinant" indicates a construct which either does not exist naturally or which has been manipulated or cloned or rearranged so that it is e.g., flanked by sequences which do not naturally flank said sequence.

In the present description, the terms "nucleic acid" or "nucleotide sequence" are used interchangeably and refer to a nucleic acid molecule having a determined sequence, which may be deoxyribonucleotide (DNA) and/or ribonucleotide (RNA). The nucleotide sequence may be first prepared by e.g., recombinant, enzymatic and/or chemical techniques, and subsequently replicated in a host cell or an in vitro system. A nucleotide sequence preferentially comprises an open reading frame encoding a product of interest, such as a polypeptide (e.g., a peptide, protein, etc) or an RNA. The nucleotide sequence may contain additional sequences such as a transcription terminator, a signal peptide, an IRES, an intron, etc.

The term "untranslated region" as used herein refers to a region of nucleotides that has no ORF and do not define an amino acid sequence of protein to be expressed by translation, or a region of nucleotides in which the ORF is not involved in any of transcription, translation, or protein expression.

The term "avian species" is intended to encompass all kinds of avians such as birds of the class of Ayes, i.e., vertebrate animals which are feathered, winged, bipedal, endothermic and egg-laying. In the context of the invention, avians or avian species refer more particularly to birds with economical and/or agronomical interests, such as poultry, (such as chickens and turkeys), waterfowl poultry (such as ducks and geese) and ornamental birds (such as swans and psittacines).

The term "vaccine" as used herein designates an agent which may be used to cause, stimulate or amplify an immune response in an organism.

A "product of interest" includes, without limitation, a polypeptide (e.g., a peptide, a protein, etc.) as well as an RNA (e.g., an antisense RNA, an interfering RNA, an aptamer, etc.).

An "immune response" designates the development in a host of a cellular and/or antibody-mediated immune response to a composition or vaccine of interest. Usually, an "immune response" includes the production of antibodies, B cells, helper T cells, and/or cytotoxic T cells, directed specifically to an antigen or antigens included in the composition or vaccine of interest. Preferably, the immune response is protective such that resistance to new infection will be enhanced and/or the clinical severity of the disease reduced.

Marek's Disease Viruses

Marek's Disease Viruses are avian herpes viruses. Various serotypes of MDV have been reported in the art, particularly serotype 1 Marek's disease virus, such as the CVI988/ Rispens strain, and serotype 2 Marek's disease virus, such as the SB1 strain. Preferred Marek's disease viruses of the invention are derived from serotypes or strains that are non-pathogenic to targeted animal (e.g., avian) species. A most preferred MDV of the invention is a recombinant MDV of serotype 1.

MDV are disclosed in publications (see for instance Kingham et al. "*The genome of herpesvirus of turkeys: comparative analysis with Marek's disease viruses*"—Journal of General Virology (2001) 82, 1123-1135) and generally available from collections. The sequence of the genome of MDV is also available in gene libraries (GenBank Acc. No. DQ530348 and AF291866).

The invention relates to any rMDV product or composition wherein a recombinant nucleotide sequence is operably linked to a beta actin-derived promoter. Indeed, the inventors have shown that such constructs allow highly improved expression and induction of strong protective immunity. The invention further shows that such viruses are compatible for combined use with distinct avian herpes viruses, to induce improved immune response against distinct antigenic pathogens without substantial cross-interference. As demonstrated in the examples, the inventors have surprisingly found that, in the context of a rMDV, this promoter causes higher and long lasting expression of a polypeptide, and that such expression is not altered by co-administration of a distinct avian herpes virus vector, thereby allowing concomitant immunization against several distinct antigens.

The Beta Actin Promoter

The sequence of chicken Beta actin promoter has been reported in the art and is available on public gene libraries. An illustrative sequence is represented in SEQ ID NO: 12.

A promoter "derived" from a chicken beta actin promoter is a promoter that comprises a sequence of a functional fragment of a chicken beta actin promoter, preferably a sequence of a transcriptionally active fragment of a chicken beta actin promoter. The promoter may further comprise additional residues or functional domains, which may be artificial and/or obtained from distinct promoter(s). A promoter derived from a chicken beta actin promoter typically comprises at least 50 consecutive nucleotides of the sequence of said chicken beta actin promoter, or a sequence having at least 90% sequence identity thereto, preferably at least 96, 97, 98 or 99% sequence identity thereto, and exhibits transcriptional activity either alone or when combined with a further domain.

The chicken beta actin-derived promoter sequence for use in the present invention is more preferably a sequence that comprises at least a core sequence of a chicken beta actin promoter. The core sequence is typically located within the region between nucleotides −1200 to −900 of the native promoter, even more preferably between nt −1192 and −922. A specific example of a core sequence of a chicken beta actin promoter is presented in SEQ ID NO: 5:

```
TATTTTGTGCAGCGATGGGGGCGGGGGGGGGGGGGGCGCGCGCCAG

GCGGGGCGGGGCGGGGCGAGGGGCGGGGCGGGGCGAGGCGGAGAGG

TGCGGCGGCAGCCAATCAGAGCGGCGCGCTCCGAAAGTTTCCTTTT

ATGGCGAGGCGGCGGCGGCGGCGGCCCTATAAAAAGCGAAGCGCGC

GGCGGGCGGGAGTCGCTGCGCGCTGCCTTCGCCCCGTGCCCCGCTC

CGCCGCCGCCTCGCGCCGCCCGCCCCGGCTCTGACTGACCGCGT
```

In a particular embodiment, the promoter used in the invention contains a core sequence of a chicken beta-actin promoter which comprises (i) SEQ ID NO: 5 or (ii) a sequence having at least 90% sequence identity to SEQ ID NO: 5, preferably at least 96, 97, 98 or 99% sequence identity to SEQ ID NO: 5, and exhibiting transcriptional promoter activity.

In a particular embodiment, the invention relates to a rMDV comprising a nucleic acid operably linked to a promoter comprising SEQ ID NO: 12.

In another particular embodiment, the invention relates to a rMDV comprising a nucleic acid operably linked to a promoter comprising SEQ ID NO: 5.

Polypeptide of Interest

The rMDV of the invention may be used to deliver and/or express any polypeptide of interest such as biologically active polypeptides or immunogenic (i.e., antigenic) polypeptides. In a preferred embodiment, the polypeptide of interest is an antigenic peptide, even more preferably a peptide or polypeptide derived from an antigen of a pathogenic organism capable of causing an infection in an animal, particularly an avian. Examples of pathogens that cause infection in avian include viruses, bacteria, fungi, protozoa, etc. The immunogenic (poly)peptide may preferably be (derived from) a surface protein, a secreted protein, or a structural protein of said pathogen, or fragments thereof. The polypeptide can be derived from any source, e.g., viral, prokaryotic, eukaryotic or synthetic.

In a preferred embodiment, the nucleic acid encodes an antigenic peptide of a bird pathogenic agent.

Specific examples of pathogenic agents include, without limitation, avian influenza virus, avian paramyxovirus type 1, also called Newcastle disease virus (NDV), avian metapneumovirus, Marek's disease virus, Gumboro disease virus, also called infectious bursal disease virus (IBDV), Infectious laryngotracheitis virus (ILVT), Infectious bronchitis virus (IBV), *Escherichia coli, Salmonella* species, *Pasteurella multocida, Riemerella anatipestifer, Ornithobacterium rhinotracheale, Mycoplasma gallisepticum, Mycoplasma synoviae*, Mycoplasmas microorganisms infecting avian species or coccidian.

Preferentially, the immunogenic polypeptide is selected from the F protein of NDV, the VP2 protein of IBDV, the gB protein of ILTV, the 40K protein of *Mycoplasma gallisepticum*, and the surface protein hemagglutinin (HA) of the avian influenza virus, or immunogenic fragments thereof.

Within the context of the invention, the term "fragment" of a protein designates preferably a fragment comprising at least 5 consecutive amino acid residues of said protein, even more preferably from 5-100. In a preferred embodiment, such a fragment comprises at least one epitope and/or is immunogenic in vivo, i.e., can cause production of antibodies that bind the full length protein.

Specific examples of immunogenic peptides include, for instance, a peptide comprising amino acid residues 1-453 of entire VP2.

Virus Construction

Gene cloning and plasmid construction are well known to one person of ordinary skill in the art and may be essentially performed by standard molecular biology techniques (*Molecular Cloning*: A Laboratory Manual. 4th Edition, Cold Spring Harbor Laboratory, Cold Spring Harbor, N.Y., USA, 2012).

As indicated above, the rMDVs of the invention comprise a recombinant sequence cloned typically into a nonessential region of the viral genome. The cloning may be accomplished by techniques know per se in the art. Typically, the recombinant viruses may be prepared by homologous recombination between the viral genome and a construct (e.g., a plasmid) comprising the nucleic acid to be inserted, flanked by nucleotides from the insertion site to allow recombination. Cloning can be made with or without deletion of endogenous sequences. In a particular embodiment, the recombinant sequence is cloned in replacement of at least part of a sequence of the genome, such as at least 50 nucleotides or more. Such deletion e.g., increases the cloning capacity of the vector.

For that purpose, a sequence containing the targeted region is typically first cloned into a suitable vector. According to the invention, such target region is preferably a region non-essential for virus replication or infection, such as a non-coding (or untranslated) region, or a nonessential gene. A preferred example of such a region is US2 gene. Examples of vectors include plasmids, such as pBR322, pBR325, pBR327, pBR328, pUC18, pUC19, pUC7, pUC8, or pUC9; phages such as lambda phage and M13 phage; or cosmids such as pHC79.

The target region sequence is integrated into the vector according to a conventional cloning method. The target region sequence used is preferably of sufficient length so as to allow subsequent in vivo homologous recombination with the viral genome. Preferably, the cloned target region sequence shall have at least approximately 100 nucleotides in length, typically above 300, such as between 1000 and 2000 nucleotides.

The coding and promoter sequences, for insertion into the virus, are inserted into the target region of the viral genome cloned in the vector. Insertion shall be made preferably in a manner that leaves a portion of sequence of the target region on each side of the cloned insert of a length sufficient to allow homologous recombination (e.g. of at least 50 nucleotides, preferably of at least 100 nucleotides). The coding and promoter sequences can be introduced into the cloned target region by classical restriction enzyme and ligation procedures. If appropriate, mutation(s) may be carried out at a specific site of the target region to create a new cleavage site for a restriction enzyme. Conventional mutagenesis techniques well known by a person skilled in the art may be used for that purpose, such as e.g., in vitro mutagenesis or PCR.

Vectors in which the coding and promoter sequence has been inserted into the target region obtained as above may be introduced into an MDV-infected cell or MDV genome-transfected cells using known techniques such as electroporation, calcium phosphate, lipofectin-based method, or the like. The recombinant viruses are thereby produced by recombination in said cells between the homologous regions of MDV-DNA and the vector. When the amount of the vector is in the range of 0.1 to 1000 μg, the efficiency of generation of recombinant viruses is particularly optimized.

The resulting recombinant virus may be selected genotypically or phenotypically using known techniques of selection, e.g., by hybridization, detecting enzyme activity encoded by a gene integrated along with the recombinant nucleic acid sequences or detecting the antigenic peptide expressed by the recombinant virus immunologically. The selected recombinant virus can be cultured on a large scale in cell culture after which, recombinant virus containing peptides can be collected.

Preferred rMDVs

Preferred rMDVs of the invention comprise at least one recombinant nucleic acid inserted into the US2 gene, more preferably in replacement of at least part of the US2 gene, even more preferably between $248^{th}$ and $494^{th}$ nucleotides from the start codon.

Most preferred rMDVs of the present invention are based on serotype 1 MDV.

Furthermore, preferred rMDVs of the invention encode an antigenic peptide selected from the F protein of NDV, the VP2 protein of IBDV, the gB protein of ILTV, the 40K protein of *Mycoplasma gallisepticum*, and the surface protein HA of the avian influenza virus, or fragments thereof.

According to a particular embodiment, the invention relates to a recombinant MDV1 which comprises, inserted in the US2 gene, a nucleotide sequence encoding a VP2 protein of IBDV, or a fragment thereof, under the control of a promoter comprising a core sequence of chicken beta actin promoter.

Specific examples of such rMDVs of the invention include RR013, RR030 and RR031.

In RR013, the antigen peptide sequence is located under the control of a Bac promoter of SEQ ID NO: 12, inserted in US2 gene of MDV1.

In RR030 and RR031, the antigen peptide sequence is located under the control of Coa5 promoter of SEQ ID NO: 5, inserted in US2 gene of MDV1.

Cell Cultures

The recombinant viruses of the present invention may be propagated in any competent cell cultures. After required growth of the viruses is achieved, the cells may be detached from the wells using a scraper or with trypsin and the infected cells may be separated from the supernatant by centrifugation.

Examples of competent cells include CEF, embryonated egg, chicken kidney cell, and the like. The cells or viruses may be cultured in a culture medium such as Eagle's MEM, Leibowitz-L-15/McCoy 5A (1:1 mixture) culture medium at about 37° C. for 3 to 6 days. The infected cells are typically suspended in a culture medium containing 10% dimethyl sulfoxide (DMSO) and stored frozen under liquid nitrogen.

Compositions and Vaccines

The invention also relates to compositions, such as vaccines, which comprise one or more recombinant MDV of the invention.

Compositions of the invention may comprise the rMDV in a pharmaceutically or veterinary acceptable vehicle or excipient. The composition may, in addition or alternatively, comprise a suitable adjuvant.

The rMDVs of the invention may be used in live form (e.g., to prepare live vaccines) or, alternatively, in inactivated, attenuated, or killed form. The production of such forms is known in the art.

The vaccine according to the present invention may further comprise a suitable solvent, such as for example an aqueous buffer or a phosphate buffer. Preferably, the vaccine also comprises additives. Additives of the present invention may be obtained from any of a number of sources including various proteins and peptides derived from animals (e.g., hormones, cytokines, co-stimulatory factors), and novel nucleic acids derived from viruses and other sources (e.g., double stranded RNA, CpG), and the like which are administered with the vaccine in an amount sufficient to enhance the immune response. In addition, any number of combinations of the aforementioned substances may provide an immunopotentiation effect, and therefore, can form an immunopotentiator of the present invention.

The vaccines of the present invention may further formulated with one or more further additives to maintain isotonicity, physiological pH and stability, for example, a buffer such as physiological saline (0.85%), phosphate-buffered saline (PBS), citrate buffers, Tris(hydroxymethyl aminomethane (TRIS), Tris-buffered saline and the like, or an antibiotic, for example, neomycin or streptomycin, etc.

The route of administration can be any route including oral, ocular (e.g., by eyedrop), oculo-nasal administration using aerosol, intranasal, Cloacal in feed, in water, or by spray, in ovo, topically, or by injection (e.g., intravenous, subcutaneous, intramuscular, intraorbital, intraocular, intradermal, and/or intraperitoneal) vaccination. The skilled person will easily adapt the formulation of the vaccine composition for each type of route of administration.

Each vaccine dose may contain a suitable dose sufficient to elicit a protective immune response in avian species. Optimization of such dose is well known in the art. The amount of antigen per dose may be determined by known methods using antigen/anti-body reactions, for example by the ELISA method.

The vaccines of the invention can be administered as single doses or in repeated doses, depending on the vaccination protocol.

The vaccines of the present invention are further advantageous in that they confer to bird species up to 80% protection against the targeted avian pathogens.

The present invention further relates to the use of the vaccine as described above for immunizing avian species, such as poultry, and to method of immunizing avian species by administering an immunologically effective amount of the vaccine according to the invention. The vaccine may be advantageously administered intradermally, subcutaneously, intramuscularly, orally, in ovo, by mucosal administration or via oculo-nasal administration.

The present invention further relates to vaccination kits for immunizing avian species which comprises an effective amount of the multivalent vaccine as described above and a means for administering said components to said species. For example, such kit comprises an injection device filled with the vaccine according to the invention and instructions for intradermic, subcutaneous, intramuscular, or in ovo injection. Alternatively, the kit comprises a spray/aerosol or eye drop device filled with the vaccine according to the invention and instructions for oculo-nasal administration, oral or mucosal administration.

Further aspects and advantages of the invention will be disclosed in the following experimental section, which is illustrative of the claimed invention.

EXAMPLES

In the experiments, several recombinant viruses have been produced and used, which are designated as follows (virus/insertion site/inserted genes):
RR013: Rispens/US2/Bac-VP2stc
RR024: Rispens/US2/RSV-VP2stc
RR025: Rispens/US2/SV40-VP2stc
RR030: Rispens/US2/Coa5-VP2stc
RR031: Rispens/US2/Coa5-VP2stc2
FW023 (recombinant HVT/IBD control): HVT/UL45-46/Bac-VP2stc
FW029 (recombinant HVT/ND control): HVT/UL45-46/Pec-F Example 1: Construction of Homology Vectors The plasmid construction was essentially performed by the standard molecular biology techniques (Molecular Cloning: A Laboratory Manual. 4th Edition, Cold Spring Harbor Laboratory, Cold Spring Harbor, N.Y., USA, 2012).
Construction of pRisUS2Sfi
A 2.2-kb DNA fragment of Rispens genome flanking the intended insertion site (within US2 gene) was cloned by PCR reactions, deleting a portion (0.2-kb) of the US2 gene and adding SfiI recognition site at the insertion site (FIG. 1). Briefly, using DNA extracted from Rispens as a template, two PCR reactions were conducted. Primer pairs used are SEQ NO. 1 (5'-AAACGAATTCGAAGCTTGCATGC-CCCGCTAAGGAC-3') and SEQ NO. 2 (5'-GCCACCA-GATGGAACTGGGGCCAATAAGGCCGGTATGC-CGTGGGCC-3'), and SEQ NO. 3 (5'-GGCCCACGGCATACCGGCCTTATTGGCCCCAGTTC CA TCTGGTGGC-3') and SEQ NO. 4 (5'-GATTACGAAT-TCGCCCTTTTACATGCTGC CCCAA-3'). Another PCR reaction was conducted using a mixture of PCR products from the two previous PCR reactions as a template and SEQ NO. 1 and SEQ NO. 4 as primers. An obtained PCR fragment was cloned into pUC18 vector (GenBank Acc. No. L09136) after digestion with EcoRI and HindIII, resulting in pRisUS2Sfi.
Construction of the Homology Vectors
Utilizing the plasmid pRisUS2Sfi, various homology vectors containing a promoter and IBDV VP2 gene from standard challenge strain (VP2-STC) were constructed. These homology vectors were used to construct recombinant Rispens/IBD (RR013, RR024, RR025, RR030, and RR031). First, pRisUS2Sfi was cleaved with SfiI and dephosphorylated with Alkaline Phosphatase *Shewanella* sp. S1B1 Recombinant (PAP) (Funakoshi #DE110). The Bac promoter-VP2-STC cassette was obtained by BglI digestion of p45/46bacVP2-STC#11 (U.S. Pat. No. 6,764,684) and inserted into the SfiI-digested pRisUS2Sfi, resulting in pRisUS2bacVP2stc. This plasmid, pRisUS2bacVP2stc, was used to construct a recombinant Rispens/IBD, RR013. Homology plasmids containing a partial core sequence (SEQ No. 5) of Bac promoter (Coa5 promoter) were also constructed. The Coa5 promoter was obtained from the plasmid pGICOA (U.S. Pat. No. 6,866,852) by BglI and XbaI digestion, and ligated with an XbaI-EcoRI fragment (6.3-kb) and an EcoRI-BglI fragment (0.1-kb) of p45/46bacVP2-STC#11, resulting in p45/46COA5VP2-STC#11. The Coa5 promoter-VP2-STC cassette was then cut out from p45/46COA5VP2-STC#11 by BglI digestion and ligated with the SfiI-digested pRisUS2Sfi, resulting in pRisUS2Coa5VP2stc. This plasmid, pRisUS2Coa5VP2stc was used to construct RR030. Another homology vector with the Coa5 promoter was constructed having a different sequence between the Coa5 promoter and the VP2-STC gene. After PCR using pRisUS2Coa5VP2stc as a template and SEQ No. 6 (5'-GTGGGGACCCGAGGATTTTG-3') and SEQ No. 7 (5'-GCGTCTAGA GGATCGATCCACCG-GTCGCCACCATGACAAACCTGCAAGATCA-3') as primers, an obtained DNA fragment was digested with XbaI and SalI, and then inserted into an XbaI-SalI fragment (5.2-kb) of pRisUS2Coa5VP2stc. The resultant plasmid, pRisUS2Coa5VP2stc2, was used to make RR031. A RSV promoter-VP2-STC cassette and a SV40 promoter-VP2-STC cassette were obtained by digestion of p44-

45d46RsvVP2 and p44-45d46SV40VP2 (EP patent 12305390), respectively, with BglI. These fragments were ligated with the SfiI-digested pRisUS2Sfi, resulting in pRisUS2RSVVP2stc and pRisUS2SV40VP2stc. These plasmids were used to construct RR024 and RR025, respectively.

Example 2: Construction of Recombinant Rispens

Construction of recombinant Rispens was conducted by homologous recombination either in cultured cells or *E. coli*. For homologous recombination in cultured cells, viral DNA of wild type Rispens virus was prepared as described by Morgan et al. (Avian Diseases, 34:345-351, 1990). Approximately 2 μg of the Rispens DNA and 1 μg of one of the homology vector were transfected into approximately $10^7$ CEF cells by electroporation using Nucleofector II (Lonza, Basel, Switzerland). The transfected cells were added to Leibovitz's L-15 (Life Technologies Corp., Cat. #41300-39), McCoy's 5A Medium (Life Technologies Corp., Cat. #21500-061) (1:1) and 4% calf serum [LM (+) medium], planted in 96-well tissue culture plates, and then incubated at 37° C. in 4-5% $CO_2$ for 5-7 days until Rispens plaques became visible. The cells were then detached from the plates by trypsinization, transferred equally to two 96-well plates with CEF, and incubated for 4 to 6 days until plaques were observed. Screening was conducted by the black plaque assay, staining only plaques expressing IBDV VP2 protein. Briefly, one of the two plates was fixed with methanol: acetone mixture (1:2) and incubated with anti-IBDV VP2 monoclonal antibody R63 (ATCC #: HB-9490). Next, incubated with biotinylated anti-mouse IgG antibody (Vector Laboratories, Cat# BA-9200) and then with VECTASTAIN ABC-AP kit (Vector Laboratories, Cat# AK-5000), plaques expressing VP2 protein were stained by addition of NBT/BCIP solution (Roche Applied Science, Cat#1681451). Wells containing stained recombinant plaques were identified and cells from the corresponding wells on the other 96-well plate were trypsinized. The cells were then diluted in fresh secondary CEF cells and transferred to 96-well plates to complete the first round of purification. The purification procedure was repeated until all plaques were stained positively in the black plaque assay. For homologous recombination in *E. coli*, DH10B *E. coli* strain carrying Rispens genome as bacterial artificial chromosomes (BAC) and plasmid pKD46 (GenBank Acc. No. AY048746) was transfected with 1 μg of one of the homology vector after induction of recombination enzymes by addition of 10 mM L-arabinose. Transfection was conducted by electroporation using Gene Pulser Xcell (Bio-Rad Laboratories) at 1.75 kV, 25 μF, and 200 ohm. After transfection, the *E. coli* was planted onto Luria-Bertani (LB) agar plates, and incubated overnight at 37° C. *E. coli* clones carrying an appropriate insert containing the VP2 gene were identified by PCR using a primer pair amplifying a region between VP2 gene and the insertion site region of Rispens genome. The primers are SEQ NO. 6 and SEQ NO. 8 (5'-TGAACTACACAAA ATTGATACTGA-3'). Rispens BAC DNA was extracted from clones that contained the insert and transfected into CEF using Nucleofector II (Lonza). The transfected CEF was planted in 96-well plates and incubated at 37° C. in 4-5% $CO_2$ for 5-7 days until Rispens plaques became visible. Plaques expressing VP2 protein were purified as described above.

Example 3: Verification of Genome Structure

Genome structures of the recombinant Rispens/IBD were verified by two PCR reactions amplifying junction regions (Junction 1 and Junction 2) at each end of the inserted genes. FIG. 2 shows where Junction 1 and Junction 2 are located in the recombinant virus genome. The primer pairs used in the PCR reactions are SEQ NO. 9 (5'-GAGGCGGACG-TAAATGGAGA-3') and SEQ NO. 8 for Junction 1, and SEQ NO. 10 (5'-GCCAGGGAATCCAGGGAAAAAGAC-3') and SEQ NO. 11 (5'-TATGAGCGGCAGTTATCGTGT-3') for Junction 2. Expected sizes of PCR products were observed with all of the recombinant Rispens, confirming that these recombinant Rispens have the expected genome structures.

Example 4: Expression of an Inserted Antigen by Recombinant Rispens

Expression of the VP2 protein by the recombinant Rispens/IBD was confirmed by the black plaque assay and the Western blot assay. Procedures for the black plaque assay are described in Experiment 2. The western blot was conducted using CEF cells infected with the recombinant viruses and anti-IBDV VP2 monoclonal antibody R63. Briefly, CEF cells in 6-well plates were infected with one of the recombinant viruses or the parent Rispens strain at a multiplicity of infection of approximately 0.1. Three days post inoculation, cells were harvested with trypsin and centrifuged at 913×g for 5 minutes. The pellet was washed with PBS and resuspended with 100 μl of PBS. After adding the same volume of 2×SDS sample buffer (130 mM Tris-Cl (pH6.8), 6% SDS, 20% Glycerol, 10% 2-Mercaptoethanol and 0.01% Bromo Phenol Blue), cell suspension was boiled for 5 minutes. The samples were separated by SDS-PAGE using 12% polyacrylamide gel and transferred to a PVDF membrane (Immobilon-P, Millipore). The membrane was dried completely and then incubated with the R63 monoclonal antibody. After the R63 antibody was washed off, biotinylated anti-mouse IgG antibody (Vector Laboratories, Cat# BA-9200) and then with VECTASTAIN ABC-AP kit (Vector Laboratories, Cat# AK-5000). Protein bound with the R63 monoclonal antibody was visualized by addition of NBT/BCIP solution (Roche Applied Science, Cat#1681451). As shown in FIG. 3, protein bands of 40 kilodaltons (kDa), which was the expected size of the VP2 protein, was observed only in the lanes with the recombinant virus infected cells. Recombinant Rispens with an entire or a partial Bac promoter, i.e. RR013, RR030, and RR031, expressed more VP2 protein than RR024, which has a RSV promoter.

Example 5: Efficacy of Recombinant Rispens in Chickens—the Beta Actin Promoter Provides Highly Superior Protection Efficacy of the recombinant Rispens viruses expressing the IBDV VP2 gene was evaluated against virulent IBDV challenge. Three recombinant Rispens/IBD viruses (RR013, RR024 and RR025) were used is which expression of the antigen is driven by different promoters. Specific pathogen free (SPF) white leghorn chickens at one day of age were divided into six groups and chicks in Groups 3 through 5 were vaccinated subcutaneously with approximately 3000 plaque forming units (pfu)/0.2 ml of one of the recombinant Rispens (Group 3, RR013: Group 4, RR024: Group 5, RR025). Chicks in Group 6 were vaccinated with FW023 (rHVT/IBD-STC#11: U.S. Pat. No. 6,764,684), which was a recombinant HVT/VP2 control. Chicks in Group 1 (non-immunized, non-challenged negative control) and chicks in Group 2 (non-immunized, challenged positive control) were left unvaccinated. The chickens were bled each week between 2 and 7 weeks of age for evaluation of humoral immunity against IBDV. Anti-IBDV antibodies were quantitated with a commercial IBDV ELISA kit (Idexx Laboratories, FlockChek IBD). At 7 weeks of age, all chickens except Group 1 were challenged with $10^3$ mean embryo infectious dose ($EID_{50}$) of virulent IBDV standard challenge (STC) strain via oral route. Chickens were observed daily for clinical signs associated with IBD, such as depression and death. Seven days post challenge, chickens were necropsied and observed for grossly observable bursal lesions such as edema, discoloration, atrophy, hemorrhage, and yellow or gelatinous exudates. Weights of body and bursa were also measured at necropsy for calculation of B/B index, which is the ratio between the weight of the bursa and the body weight of challenged birds divided by the same ratio of non-challenged birds.

Table 1 summarizes the results.

TABLE 1

Protection of recombinant Rispens against virulent IBDV challenge in SPF chickens (Efficacy trial 1)

| Group number | Group | # chickens | B/B Index | # dead after challenge | # with bursal lesions/# total | % protection |
|---|---|---|---|---|---|---|
| 1 | NINC | 13 | 1.00 | 0 | 0/13 | Not applicable |
| 2 | NICC | 13 | 0.47 | 0 | 13/13 | 0% |
| 3 | RR013 | 15 | 0.95 | 0 | 2/15 | 87% |
| 4 | RR024 | 15 | 0.77 | 0 | 7/15 | 53% |
| 5 | RR025 | 15 | 0.59 | 0 | 10/15 | 33% |
| 6 | FW023 | 13 | 0.93 | 0 | 1/13 | 92% |

NINC = non-immunized, non-challenged negative controls
NICC = non-immunized, challenged positive controls
RR013: Rispens/US2/Bac-VP2stc
RR024: Rispens/US2/RSV-VP2stc
RR025: Rispens/US2/SV40-VP2stc
FW023 (recombinant HVT/IBD control): HVT/UL45-46/Bac-VP2stc All chickens in Group 2 (challenged positive control) developed gross bursal lesions typical of IBD, while all chickens in Group 1 (non-challenged negative control) remained free from such lesions. Protection provided by RR013 (Group 3) was 87% (13/15) and it was equivalent to protection from FW023 recombinant HVT/IBD control (Group 6). B/B Index of group 3 was 0.95, suggesting no significant atrophy in bursa. Surprisingly, RR024 (Group 4) and RR025 (Group 5) gave only partial protections (53% and 33%). All vaccinated groups gave higher IBD ELISA titers starting from 3 weeks of age (FIG. 4).

Titers in RR013 vaccinated chickens were consistently higher than those in RR024 or RR025 vaccinated chickens, which is consistent with protection results after challenge.

In conclusion, RR013 with a Bac promoter, provided substantially superior humoral and protective immunity as compared to RR024 and RR025, both of which contain non-Bac promoters.

Example 6: Efficacy of Recombinant Rispens in Chickens—Activity of Different Beta Actin-Derived Promoters The efficacy of RR013, RR030, and RR031, all of which contain an entire or a partial Bac promoter, was investigated in commercial layer (white leghorn) chickens with maternal antibodies. Chickens at one day of age were divided into six groups and chicks in Groups 3 through 5 were vaccinated subcutaneously with approximately 3000 plaque forming units (pfu)/0.2 ml of one of the recombinant Rispens (Group 3, RR013: Group 4, RR030: Group 5, RR031). Chicks in Group 6 were vaccinated with FW023, which was a recombinant HVT/VP2 control. Chicks in Group 1 (non-immunized, non-challenged negative control) and chicks in Group 2 (non-immunized, challenged positive control) were left unvaccinated. The chickens were bled each week between 1 and 7 weeks of age and tested for presence of anti-IBDV antibodies with a commercial IBDV ELISA kit (IDEXX IBD Ab Test: IDEXX Laboratories). Challenge was conducted two times at 5 weeks of age and 7 weeks of age. A half of the chickens in each group were challenged at 5 weeks of age and the other half were challenged at 7 weeks of age. For challenge, $10^3$ $EID_{50}$ of virulent IBDV STC strain was administered via oral route. Observation and evaluation after challenge were conducted in the same manner as in Example 5.

Tables 2 and 3 summarize the results.

TABLE 2

Protection of recombinant Rispens against virulent IBDV challenge at 5 weeks of age in commercial layer chickens (Efficacy trial 2)

| Group number | Group | # chickens | B/B Index | # dead after challenge | # with bursal lesions/# total | % protection |
|---|---|---|---|---|---|---|
| 1 | NINC | 20 | 1.00 | 0 | 0/20 | Not applicable |
| 2 | NICC | 22 | 1.08 | 3 | 22/22 | 0% |
| 3 | RR013 | 20 | 1.09 | 0 | 2/20 | 90% |
| 4 | RR030 | 22 | 1.08 | 0 | 1/22 | 95% |
| 5 | RR031 | 22 | 1.21 | 0 | 1/22 | 95% |
| 6 | FW023 | 21 | 1.24 | 1 | 4/21 | 81% |

NINC = non-immunized, non-challenged negative controls
NICC = non-immunized, challenged positive controls
RR013: Rispens/US2/Bac-VP2stc
RR030: Rispens/US2/Coa5-VP2stc
RR031: Rispens/US2/Coa5-VP2stc2
FW023 (recombinant HVT/IBD control): HVT/UL45-46/Bac-VP2stc

TABLE 3

Protection of recombinant Rispens against virulent IBDV challenge at 7 weeks of age in commercial layer chickens (Efficacy trial 2)

| Group number | Group | # chickens | B/B Index | # dead after challenge | # with bursal lesions/# total | % protection |
|---|---|---|---|---|---|---|
| 1 | NINC | 19 | 1.00 | 0 | 0/20 | Not applicable |
| 2 | NICC | 19 | 0.55 | 5 | 19/19 | 0% |
| 3 | RR013 | 19 | 0.96 | 0 | 3/19 | 84% |
| 4 | RR030 | 22 | 0.96 | 1 | 2/22 | 91% |
| 5 | RR031 | 20 | 0.91 | 0 | 4/20 | 80% |
| 6 | FW023 | 21 | 0.97 | 1 | 4/21 | 81% |

After challenge at 5 weeks of age, all groups vaccinated with recombinant Rispens containing a BAC promoter gave excellent protection (90% for RR013, 95% for RR030, and 95% for RR031), while all of chickens in non-immunized challenged positive control (Group 2) developed gross bursal lesions typical of IBD (Table 2). FW023 recombinant HVT/IBD control gave a protection at 81%, which was lower than recombinant Rispens groups. All chickens in Group 1 (non-challenged negative control) remained free from such lesions. High B/B Index in non-immunized challenged positive control (Group 2) while exhibiting typical IBD gross lesions in bursa may indicate involvement of reminant maternally derived antibodies, leading to the delay in development of bursal lesions. After challenge at 7 weeks of age, all groups vaccinated with recombinant Rispens again containing a BAC promoter gave excellent protection (84% for RR013, 91% for RR030, and 80% for RR031), while all of chickens in non-immunized challenged positive control (Group 2) developed gross IBD bursal lesions (Table 3). B/B Indices of the vaccinated groups were above 0.91, suggesting no significant atrophy in bursa. IBDV ELISA results show that after decay of maternally derived antibodies from 1 week to 4 weeks, all vaccinated groups gave higher IBD ELISA titers (FIG. 5). Titers in RR030 and RR031 vaccinated chickens were higher than those in FW023 vaccinated chickens between 5 and 7 weeks of age.

In summary, RR013, RR030, and RR031, all of which contain an entire or a partial Bac promoter combined with the VP2 gene, gave excellent protection in commercial white leghorn layer chickens with maternal antibodies at 5 and 7 weeks of age after vaccination at one day of age.

Example 7: Stability of Recombinant Rispens of the Invention

In this example, the stability of RR030 and RR031 was evaluated in cell culture (in vitro) and in chickens (in vivo). For in vitro stability, viruses were passed in chicken embryo fibroblasts (CEF) 20 times. For in vivo stability, viruses were inoculated to one day of age commercial layer (white leghorn) chickens and then re-isolated from the vaccinated chickens at 5 and 7 weeks of age by inoculating peripheral blood lymphocytes of the chickens onto CEF. Viruses after in vitro passages and viruses isolated from vaccinated chickens were tested by PCR and the black plaque assay using R63 anti-IBDV VP2 monoclonal antibody.

PCR assay detected expected bands with all of tested samples, suggesting that there was no detectable deletion or change in the virus genome. After the black plaque assay using R63 anti-IBDV VP2 monoclonal, all plaques were stained black with all tested samples.

Therefore, RR030 and RR031 are genetically and phenotypically stable in vitro and in vivo.

Example 8: Duration of Immunity of Rispens/IBD

Figure 7:
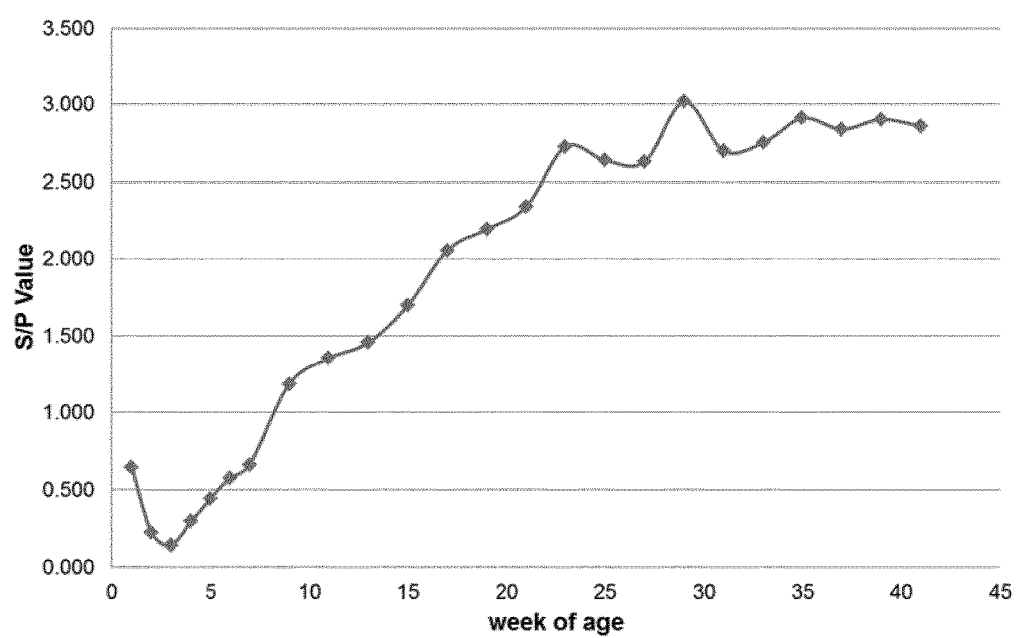
FIG. 7 illustrates the long duration of immunity to IBDV conferred by a recombinant virus of the invention.

In order to investigate duration of immunity to IBDV conferred by Rispens/IBD, chickens vaccinated with RR030 were monitored for IBDV ELISA titers through 41 weeks of age. More particularly, one day of age commercial layer (white leghorn) chickens with maternal antibodies were vaccinated subcutaneously with approximately 3000 pfu/0.2 ml of the recombinant Rispens/IBD (RR030). The chickens were bled weekly between 1 and 7 weeks of age and biweekly thereafter. Sera were tested for presence of anti-IBDV antibodies with a commercial IBDV ELISA kit (IDEXX IBD Ab Test: IDEXX Laboratories). As shown in FIG. 7, after maternal antibodies against IBDV waned through 3 weeks of age, ELISA titers started to increase. Titers continued to increase up to S/P values of more than 2.5 through 25 weeks of age, and high level of IBD ELISA titers were maintained through 41 weeks of age. This result demonstrates that Rispens/IBD provides exceptionally long duration of immunity against IBDV.

Example 9: Efficacy of Recombinant Rispens in Chickens—No Interference with Distinct HVT In this example, the compatibility between recombinant Rispens/IBD (RR030) containing a BAC promoter and recombinant HVT/ND (FW029) (rHVT/NDV: U.S. Pat. No. 6,866,852) was investigated. One day of age commercial layer (white leghorn) chickens with maternal antibodies were divided into six groups and vaccinated. Group 1 was vaccinated subcutaneously with approximately 3000 pfu/0.2 ml of the recombinant Rispens/IBD (RR030) alone. Group 2 received a mixture of RR030 and recombinant HVT/ND (FW029), both at 3000 pfu/0.2 ml. A group of chicks (Group 3) was vaccinated only with FW029. Chicks in Group 4 were vaccinated with FW023, which was a recombinant HVT/VP2 control. Chicks in Group 5 (non-immunized, challenged positive control) and in Group 6 (non-immunized, non-challenged negative control) were left unvaccinated. The chickens were bled each week between 2 and 7 weeks of age and tested for presence of anti-IBDV antibodies with a commercial IBDV ELISA kit (IDEXX IBD Ab Test: IDEXX Laboratories) and for presence of anti-NDV antibodies with a commercial NDV ELISA kit (IDEXX NDV Ab Test: IDEXX Laboratories). Challenge with either virulent IBDV or virulent NDV was conducted at 7 weeks of age. All of the chickens in Group 1 (RR030 alone) and Group 4 (FW023 alone), and a half of the chickens in Group 2 (RR030+FW029) and Group 5 (non-immunized, challenged positive control) received IBDV challenge with $10^3$ $EID_{50}$ of virulent IBDV STC strain via oral route, while all of the chickens in Group 3 (FW029 alone) and the other half of the chickens in Group 2 (RR030+FW029) and Group 5 (non-immunized, challenged positive control) received NDV challenge with $10^3$ $EID_{50}$ of very virulent (neurotropic velogenic) NDV Texas GB strain via intramuscular injection into the femoral region. Observation and evaluation after IBDV challenge were conducted in the same manner as in Example 5 and 6. For NDV challenge, the chickens were observed daily for 14 days for clinical signs typical of neurotropic velogenic ND such as depression, neurological symptoms, and deaths.

The results are summarized in Table 4.

TABLE 4

Compatibility between recombinant Rispens/IBD and recombinant HVT/NDV in commercial layer chickens (Efficacy trial 3)

| | | | IBD challenge | | ND challenge | |
|---|---|---|---|---|---|---|
| Group number | Group | # chickens | # with bursal lesions/ # total | % protection | # with ND clinical signs/# total | % protection |
| 1 | RR030 | 17 | 2/17 | 88% | N/A | N/A |
| 2 | RR030 + FW029 | 33 | 1/16 | 94% | 2/17 | 88% |
| 3 | FW029 | 17 | N/A | N/A | 2/16 | 88% |
| 4 | FW023 | 16 | 1/16 | 94% | N/A | N/A |
| 5 | NICC | 31 | 15/15 | 0% | 16/16 | 0% |
| 6 | NINC | 15 | N/A | N/A | N/A | N/A |

Figure 6A:
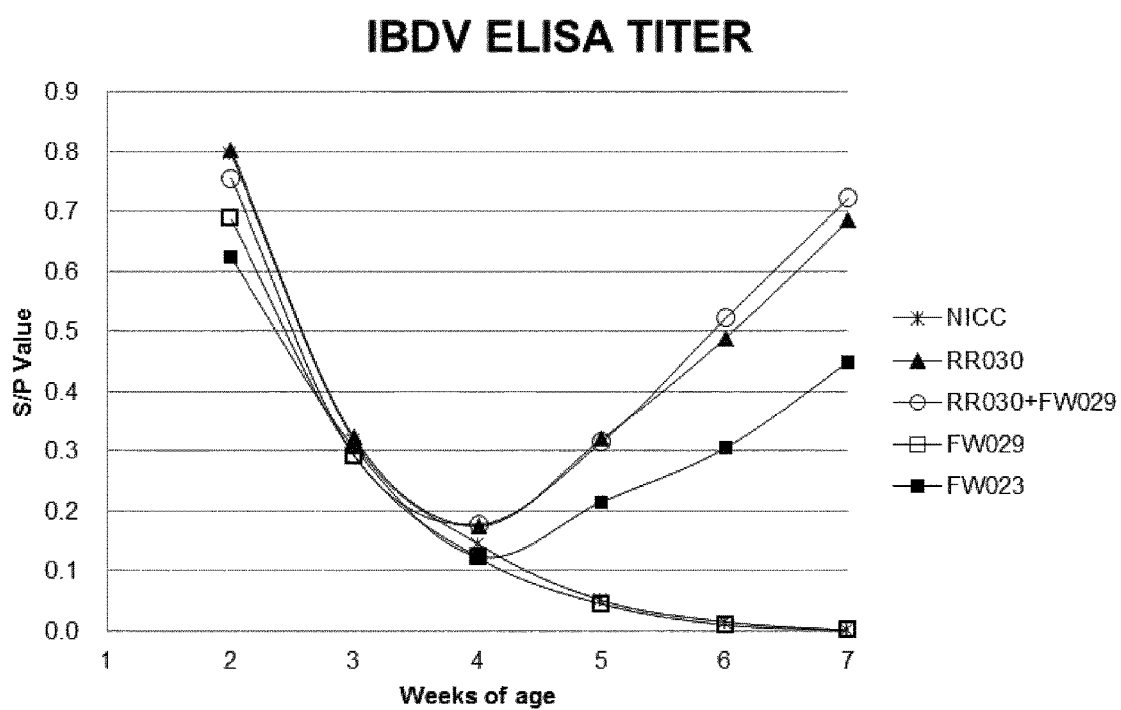
FIGS. 6A and 6B illustrates IBDV and NDV ELISA titers in commercial white leghorn chickens vaccinated with recombinant Rispens/IBD and recombinant HVT/ND using a commercial IBD ELISA kit and a commercial ND ELISA kit.
Figure 6B:
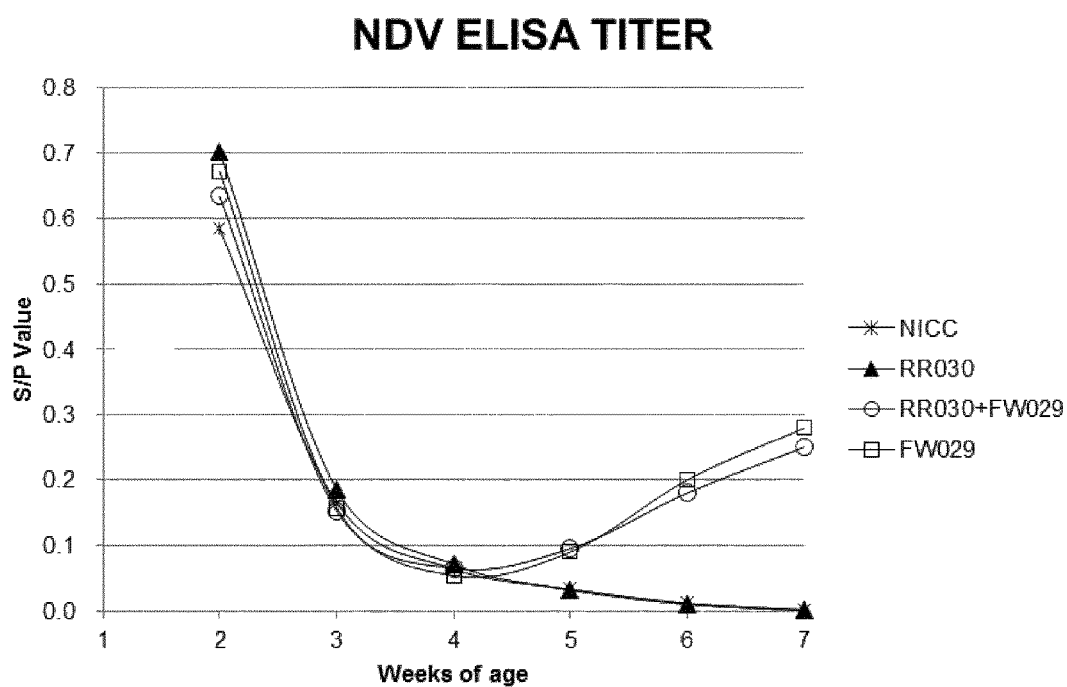

RR030: Rispens/US2/Coa5-VP2stc
FW029 (recombinant HVT/ND control): HVT/UL45-46/Pec-F
FW023 (recombinant HVT/IBD control): HVT/UL45-46/Bac-VP2stc
NICC = non-immunized, challenged positive controls
NINC = non-immunized, non-challenged negative controls RR030 combined with FW029 (Group 2) provided excellent protection against both IBD and ND challenges. After IBDV challenge, RR030 combined with FW029 (Group2) provided 94% (15/16) protection, which was equivalent to protection by RR030 alone (Group 1) at 88% (15/17) protection. In Group 4 vaccinated with FW023, 94% of the chickens were protected. All chickens in non-immunized, challenged positive control (Group 5) developed gross bursal lesions. Following NDV challenge, 88% (15/17) protection was observed with Group 2 (RR030 combined with FW029), while FW029 (14/16) alone provided 88% protection. All chickens in the challenged positive control (Group 5) showed clinical signs of ND. ELISA results also demonstrated that humoral immunity developed by RR030 or FW029 did not decrease when these two viruses were combined (FIGS. 6A and 6B).

In conclusion, this example demonstrates a lack of interference between recombinant Rispens/IBD containing a Bac construct and recombinant HVT/ND.

The invention claimed is:

1. A recombinant Marek's disease virus of serotype 1 (MDV1) which comprises (1) a promoter of 274 nucleotides in length consisting of SEQ ID NO: 5 or consisting of a sequence having at least 90% sequence identity to SEQ ID NO: 5 and exhibiting transcriptional promoter activity and (2) under the control of said promoter, a recombinant nucleotide sequence encoding a polypeptide.

2. The recombinant MDV1 of claim 1, wherein the promoter consists of SEQ ID NO: 5.

3. The recombinant MDV1 of claim 1, wherein said promoter and said recombinant nucleotide sequence are inserted into a non-essential region of the virus.

4. The recombinant MDV1 of claim 1, wherein the polypeptide is an antigenic polypeptide or peptide.

5. The recombinant MDV1 of claim 4 wherein the antigenic polypeptide or peptide is from an avian pathogen.

6. The recombinant MDV1 of claim 5, wherein the avian pathogen is selected from the group consisting of avian paramyxovirus type 1, Gumboro disease virus, infectious laryngotracheitis virus (ILTV), *Mycoplasma* galisepticum, and avian influenza virus.

7. The recombinant MDV1 of claim 6, wherein the antigenic polypeptide or peptide is the VP2 protein of infectious bursal disease virus or an immunogenic fragment thereof.

8. The recombinant MDV1 of claim 1, wherein the virus comprises a further recombinant nucleotide sequence encoding a distinct polypeptide.

9. The recombinant MDV1 of claim 1, wherein said promoter and said recombinant nucleotide sequence are inserted into a non-essential region of the virus and the promoter has at least 96% sequence identity to SEQ ID NO: 5.

10. A composition comprising a recombinant Marek's disease virus of claim 1 and, optionally, a pharmaceutically or veterinary acceptable excipient or carrier and/or a suitable adjuvant.

11. A method for vaccinating an avian, comprising administering to said avian a recombinant MDV1 of claim 1.

12. A method for vaccinating an avian, comprising simultaneous, separate sequential or alternated administration to said avian of a recombinant MDV1 of claim 1 expressing a first antigen and a distinct recombinant avian virus expressing a second distinct antigen.

13. The method of claim 12, wherein the MDV1 expresses a VP2 antigen, and the distinct avian virus is a herpesvirus of turkeys expressing a distinct antigen.

14. A method for producing a recombinant MDV1 of claim 1 comprising (i) introducing a recombinant nucleotide sequence encoding a polypeptide under the control of a promoter of 274 nucleotides in length consisting of SEQ ID NO: 5 or consisting of a sequence having at least 90% sequence identity to SEQ ID NO: 5 and exhibiting transcriptional promoter activity into a nonessential region of the genome of a MDV1 virus, (ii) optionally replicating the virus, and (iii) optionally collecting the virus.

15. The recombinant MDV1 of claim 6, wherein the antigenic peptide of avian paramyxovirus type 1 is the F protein of newcastle disease virus or a fragment thereof, the antigenic peptide of Gumboro disease virus is the VP2 protein of the infectious bursal disease virus or a fragment thereof, the antigenic peptide of the infectious laryngotracheitis virus is the gB protein or a fragment thereof, the antigenic peptide of *mycoplasma* galisepticum is the 40K protein or a fragment thereof, and the antigenic peptide of the avian influenza virus is a surface protein hemagglutinin or a fragment thereof.

16. A method for vaccinating an avian, comprising administering to said avian a composition of claim 10.

17. The method of claim 11, wherein the avian is a chicken.

18. The method of claim 12, wherein the avian is a chicken.

19. The method of claim 16, wherein the avian is a chicken.

20. The recombinant MDV1 of claim 3, wherein said promoter and said recombinant nucleotide sequence are inserted into the US2 gene of said virus.

* * * * *